(12) United States Patent
Shchervinsky

(10) Patent No.: US 6,941,174 B2
(45) Date of Patent: Sep. 6, 2005

(54) TEMPORARY PACING WIRE HAVING A CONSTRAINED ANCHOR AND METHOD OF PRODUCING SAME

(75) Inventor: Semyon Shchervinsky, Whitehouse Station, NJ (US)

(73) Assignee: Ethicon, Inc., Somerville, NJ (US)

( * ) Notice: Subject to any disclaimer, the term of this patent is extended or adjusted under 35 U.S.C. 154(b) by 446 days.

(21) Appl. No.: 10/039,191

(22) Filed: Dec. 31, 2001

(65) Prior Publication Data

US 2003/0125787 A1 Jul. 3, 2003

(51) Int. Cl.$^7$ .................................................. A61N 1/05
(52) U.S. Cl. ...................... 607/130; 607/119; 607/132; 607/129
(58) Field of Search ................................ 607/116, 120, 607/122, 125–130, 132, 149; 600/373–375, 395

(56) References Cited

U.S. PATENT DOCUMENTS

| | | | |
|---|---|---|---|
| 4,258,724 A | * | 3/1981 | Balat et al. ................. 607/128 |
| 4,341,226 A | | 7/1982 | Peters |
| 4,475,560 A | * | 10/1984 | Tarjan et al. ................ 607/128 |
| 4,633,880 A | | 1/1987 | Osypka et al. |
| H356 H | * | 11/1987 | Stokes et al. ................ 607/126 |
| 4,827,940 A | | 5/1989 | Mayer et al. ................ 600/375 |
| 4,841,971 A | * | 6/1989 | Hess .......................... 607/126 |
| 5,217,027 A | * | 6/1993 | Hermens ..................... 607/126 |
| 5,292,328 A | | 3/1994 | Hain et al. |
| 5,314,463 A | | 5/1994 | Camps et al. |
| 5,350,419 A | | 9/1994 | Bendel et al. |
| 5,480,420 A | * | 1/1996 | Hoegnelid et al. .......... 607/116 |
| 5,522,876 A | * | 6/1996 | Rusink ........................ 607/127 |
| 5,531,783 A | * | 7/1996 | Giele et al. .................. 607/126 |
| 5,551,427 A | * | 9/1996 | Altman ........................ 600/374 |
| 5,658,326 A | * | 8/1997 | Barsne ........................ 607/126 |
| 5,683,447 A | * | 11/1997 | Bush et al. .................. 607/126 |
| 5,922,015 A | * | 7/1999 | Schaldach ................... 607/126 |
| 6,055,457 A | * | 4/2000 | Bonner ....................... 607/126 |
| 6,163,728 A | * | 12/2000 | Wildon ....................... 607/132 |
| 6,217,369 B1 | | 4/2001 | Shchervinsky et al. |
| 6,330,481 B1 | * | 12/2001 | Van Wijk et al. ........... 607/129 |

* cited by examiner

*Primary Examiner*—Kennedy Schaetzle

(57) ABSTRACT

A surgical electrode has an anchor which is constrained by a coating made from a bioabsorbable material. The anchor may have a barbed harpoon-like shape designed to enhance the retention strength of the anchor.

15 Claims, 5 Drawing Sheets

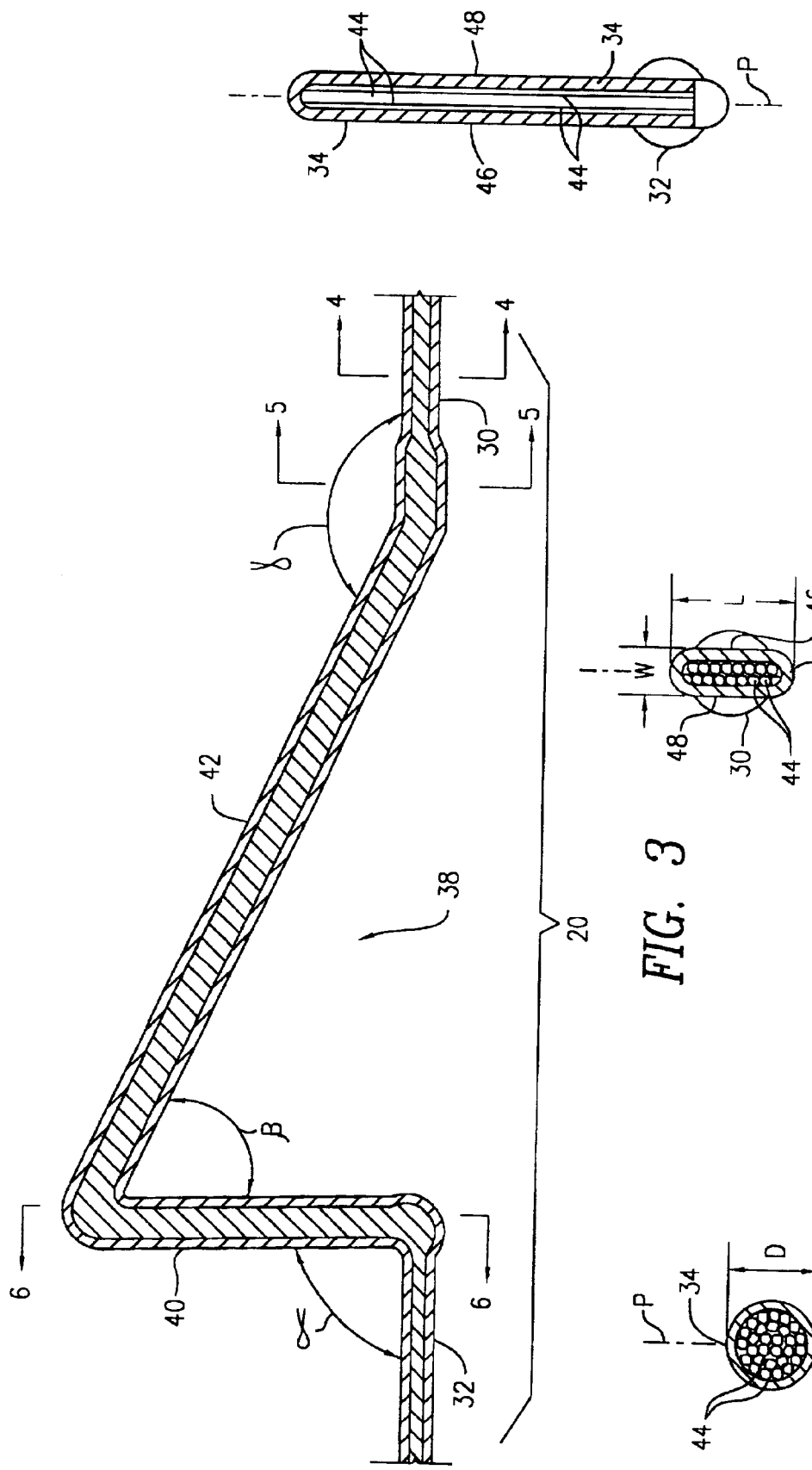

TEMPORARY PACING WIRE HAVING A CONSTRAINED ANCHOR AND METHOD OF PRODUCING SAME

FIELD OF THE INVENTION

The present invention relates to a surgical electrode, and, more particularly, to a temporary cardiac pacing wire having an anchor for anchoring the surgical electrode to a patient's heart.

BACKGROUND OF THE INVENTION

Devices to stimulate and/or regulate cardiac function are known in the prior art. Such devices typically include a power source, such as a pacemaker, and one or more surgical electrodes attached to the pacemaker and to a patient's heart. Generally, there are two types of devices to stimulate or regulate cardiac function; namely, permanent pacemakers and temporary pacemakers.

The permanent-type of pacemaker is implanted entirely within a patient's body and is intended for long-term use. The temporary pacemaker is located outside the patient's body and is connected to the heart by a surgical electrode called a "temporary pacing wire" because it is intended for short-term use (e.g., 1 to 10 days). As used herein, the phrase "temporary cardiac pacing wire" shall mean those pacing wires specifically designed and intended for short-term use within the body and not those pacing wires specifically designed and intended for chronic implant. Although surgical electrodes are used for preparing electrocardiograms and other applications, the description that follows will, for the sake of brevity, focus on temporary pacing wires.

In general, temporary pacing wires are constructed from a number of fine, stainless steel wires braided or twisted together to form a single, flexible, multi-strand electrode wire. The major portion of the wire is electrically insulated with a polyethylene, polytetrafluoroethylene, silicone, nylon, or other non-conducting coating, a short length of wire at either end being left uninsulated. To the distal end of the electrode wire, there is attached, by swaging or other means, a fine curved needle for piercing the heart tissue to place the electrode in the myocardium. At the proximal uninsulated end of the electrode wire, a straight (e.g., Keith-type) cutting needle is attached for piercing the thoracic wall to lead the electrode wire outside the body for connection with the pacemaker. Once that has been accomplished, the needle, or its sharp-pointed end, is clipped or broken off and the proximal end of the electrode wire is readied for attachment to the pacemaker as required to stimulate or regulate the beating of the heart.

During the time that the temporary pacing wire is performing its function, the distal end of the electrode must remain securely attached to the heart. The retention force must be sufficient to prevent the temporary pacing wire from being accidentally detached by the continually beating heart. When there is no longer a need to stimulate or regulate the heart, it is necessary to remove the temporary pacing wire that runs from the external pacemaker to the heart. The removal of the temporary pacing wire should be accomplished with minimal heart trauma.

DESCRIPTION OF THE RELATED ART

U.S. Pat. No. 4,633,880 to Osypka et al. discloses a surgical electrode which can be used as a temporary lead for cardiac pacing or for heart monitoring purposes. The electrode has two elongated conductors whose distal ends are provided with spaced-apart poles. One pole is defined by at least one bare strand having a shape (e.g., a zig-zag, undulate, or helical shape) which allows the strands to reduce the width of the pole during penetration into the heart wall. After penetration into the heart wall, the strands tend to increase the width of the pole to ensure reliable retention of the pole, as well as to prevent migration of the pole in the heart wall.

U.S. Pat. No. 4,341,226 to Peters and U.S. Pat. No. 5,217,027 to Hermens disclose temporary cardiac leads for establishing electrical contact between a body tissue and a pulse generator. In both patents, a helical coil, made from a biocompatible plastic, is attached to the lead for the purpose of resisting movement relative to the body tissue (e.g., myocardium tissue). Each helical coil can be elongated under the stress of tension supplied to pull the associated lead into position. The helical coil then returns to its initial shape, thereby holding the associated lead in place until removal, at which time the helical coil is again elongated. While the turns of the coil disclosed in the Peters '226 Patent have a generally circular cross-sectional shape, the turns of the coil disclosed in the Hermens '027 Patent have a generally rectangular cross-sectional shape in order to improve the positioning of the coil within the body tissue.

U.S. Pat. No. 5,350,419 to Bendel et al. discloses a cardiac pacing lead that has a conductive wire made from a single filament of a low modulus metal. An integral anchor is formed in a distal uninsulated section of the wire for anchoring the pacing lead in the myocardium of a heart. The anchor has a waveform-like shape, such as sinusoidal, square, sawtooth or gear, either full wave or half wave or combinations thereof. Although such waveform shapes are preferred, the anchor may have a variety of different shapes (e.g., a helix) which are effective to anchor the wire in the myocardium.

U.S. Pat. No. 5,314,463 to Camps et al. discloses a bipolar temporary pacing wire whose distal end has a fixation coil that is embedded in the heart wall for retaining the device in the heart. The fixation coil has a design which is similar, if not identical, to the helical coil disclosed in the Hermens '027 Patent.

SUMMARY OF THE INVENTION

The present invention involves an improved surgical electrode having an anchor which is constrained by a coating made from a bioabsorbable material. By choosing a bioabsorbable material that begins to lose its strength retention (i.e., constrainment properties) after a predetermined amount of time in a patient's body, the coating initially functions to maintain the desired shape of the anchor (e.g., a barbed harpoon-like shape) during insertion into the patient's body. As the coating subsequently loses its strength retention, the anchor becomes less constrained and therefore easier to remove.

In one embodiment, the anchor is made from a piece of multi-strand electrode wire which is void of any insulation (i.e., the electrode wire can be supplied without insulation or its electrically insulating coating is stripped therefrom). After shaping the bare electrode wire into the desired harpoon-like shape, it is coated with a bioabsorbable material which functions to constrain the resulting anchor, at least until the coating begins to lose its strength retention. Prior to coating the electrode wire with the bioabsorbable material, a barbed section of the wire can be flattened from its normally round cross-sectional shape into a non-round cross-sectional shape, such as rectangular, oval or oblong.

When, for instance, the electrode wire is used as a temporary cardiac pacing wire, the anchor increases the retention force or strength (i.e., the anchoring properties) of the pacing wire without increasing damage or trauma to the heart during insertion and removal of the pacing wire. The pacing wire can be either bipolar or monopolar.

BRIEF DESCRIPTION OF THE DRAWINGS

Further objects, features and advantages of the present invention will become apparent upon consideration of the following detailed description of an exemplary embodiment considered in conjunction with the accompanying drawings, in which:

FIG. 3 is a cross-sectional view, taken along section line 3—3 and looking in the direction of the arrows, of the anchor shown in FIG. 3;

FIG. 4 is an enlarged cross-sectional view, taken along section line 4—4 and looking in the direction of the arrows, of the anchor shown in FIG. 3;

FIG. 5 is an enlarged cross-sectional view, taken along section line 5—5 and looking in the direction of the arrows, of the anchor shown in FIG. 3;

FIG. 6 is an enlarged cross-sectional view, taken along section line 6—6 and looking in the direction of the arrows, of the anchor shown in FIG. 3;

DETAILED DESCRIPTION OF THE EXEMPLARY EMBODIMENT

Although the present invention is applicable to many different types of surgical electrodes, it is especially suitable for use in conjunction with a bipolar temporary cardiac pacing wire. Accordingly, the present invention will be described below in connection with such a pacing wire.

As used herein, the term "distal" shall mean that portion of the pacing wire or element thereof which is remote from a source of the electrical signals located external to the patient's body. Conversely, the term "proximal" shall mean that portion of the pacing wire or element thereof which is in close proximity to the external source of electrical signals.

Figure 1:
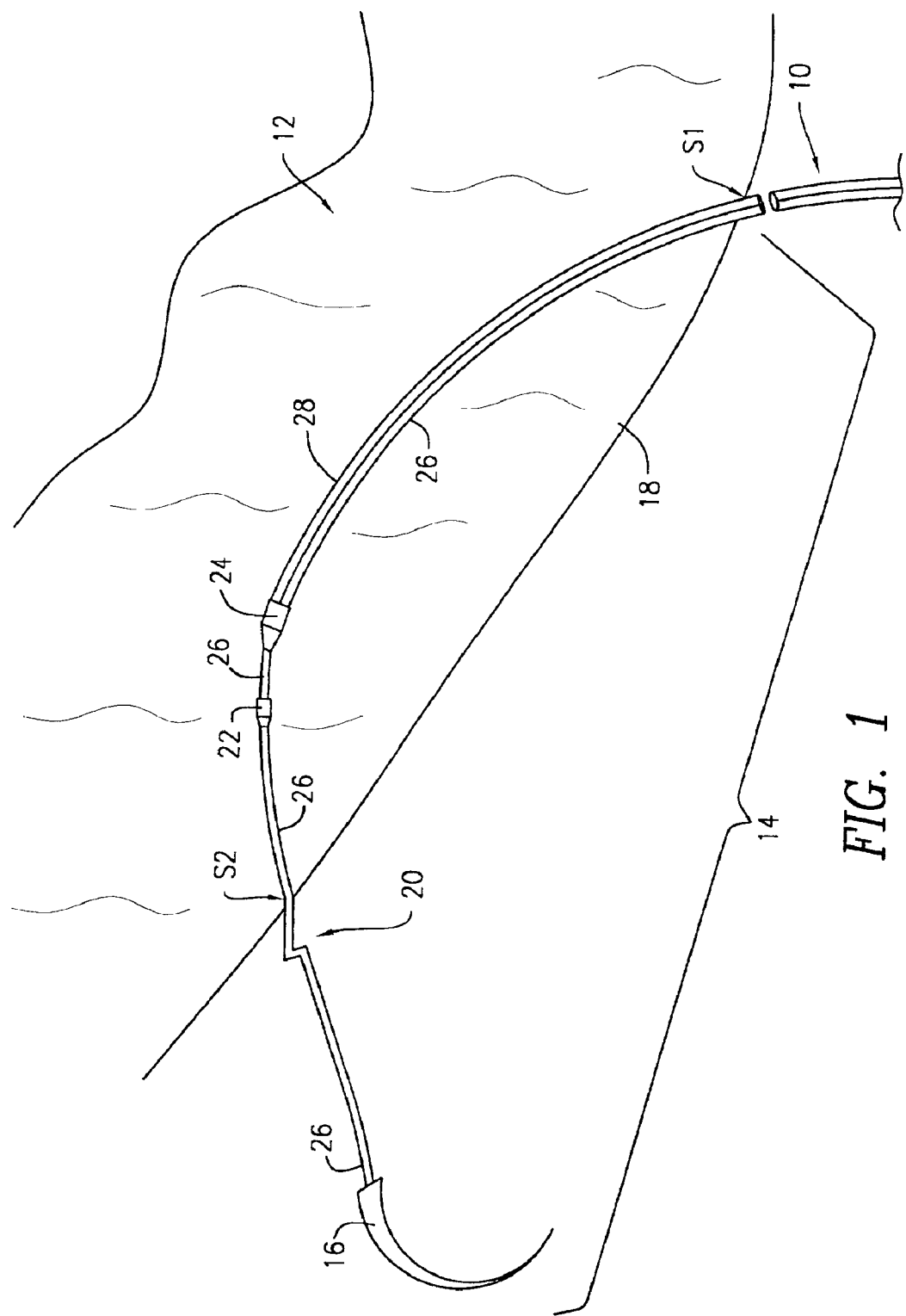
FIG. 1 is a schematic representation illustrating the use of a temporary cardiac pacing wire which is equipped with an anchor constructed in accordance with the present invention and which is attached to a patient's heart.
Figure 2:
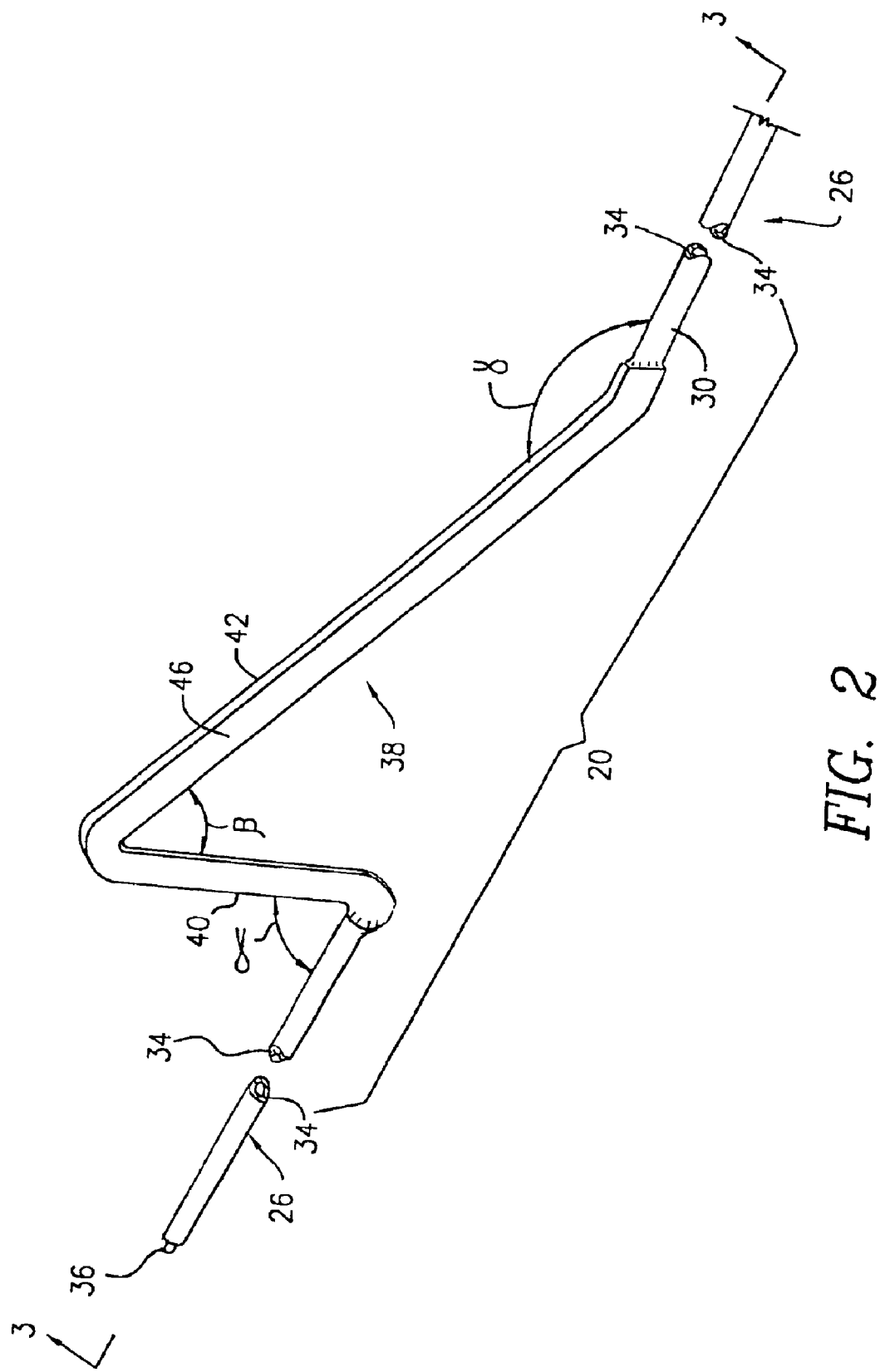
FIG. 2 is a detailed perspective view of the anchor illustrated schematically in FIG. 1.

Referring to FIG. 1, a bipolar temporary cardiac pacing wire 10 is shown immediately after its attachment to a patient's heart 12. More particularly, the pacing wire 10 includes a distal section 14, which is anchored to the heart 12, and a proximal end (not shown), which is connected to a source of electric pulses (e.g., a pacemaker) located outside the patient's body. The pacing wire 10 is attached to the heart 12 by inserting a curved needle 16 into the heart 12 at a first site (S1) and then withdrawing the needle 16 from the heart 12, through its myocardium 18, at a second site (S2). The distal section 14 of the pacing wire 10 is securely maintained in the position illustrated in FIG. 1 by an anchor 20, which abuts the heart's myocardium 18. While the anchor 20 is shown outside the heart 12 in FIG. 1, it should be understood that the anchor 20 could be located directly in the myocardium 18. Once the anchor 20 has been properly positioned relative to the heart 12, the distal section 14 is severed at a point between the anchor 20 and the needle 16. Once severed, the needle 16 is discarded.

Because the pacing wire 10 is bipolar, it has a pair of electrodes, one in the form of a conductive bushing 22 and the other in the form of a conductive bushing 24. The bushings 22, 24 are electrically connected to electrode wires 26, 28, respectively, as is customary in the cardiac pacing field. If the insulation is removed from the electrode wire 26, the wire itself could function as an electrode. Such an alternative design is not, however, desirable because it would tend to weaken the electrical pacing signal while also exposing other body tissue to such signals.

On the proximal side of the bushing 24, the electrode wires 26, 28 are arranged in side-by-side (i.e., "lamp cord") fashion, each wire having a braided, multi-strand core of stainless steel and a surrounding layer of insulation made from polyethylene. Alternatively, the core of each wire could have a twisted construction with a surrounding layer of insulation made from polyethylene or any other suitable electric non-conducting material, such as silicone, polytetrafluoroethylene, or nylon.

The bushing 24 is electrically and mechanically connected to the electrode wire 28, but only mechanically connected to the electrode wire 26, which passes through the bushing 24 and is mechanically and electrically connected to the bushing 22. The bushings 22, 24 have a conventional construction adapted to transmit electrical signals from one to the other for the purpose of stimulating, pacing, sensing, monitoring, or defibrillating the heart 12.

Normally, the electrode wire 26 has a transverse (i.e., lateral) cross-sectional shape which is generally circular. To form the anchor 20, the original insulation is stripped or otherwise removed from the portion of the electrode wire 26 distal to the bushing 22. The stripped (i.e., bare) portion of the electrode wire 26 is then placed in a fixture where it is wound between a plurality of movable pins arranged to impart a barbed harpoon-like shape to the stripped portion. After closing the fixture, it is placed between the platens of any suitable press (e.g., Carver Laboratory Press Model 2696, manufactured by Fred Carver, Inc. of Menomonee Falls, Wis.) and then flattened by the platens using a force of approximately 5,000 pounds.

The stripped portion of the electrode wire 26, which now has a flattened or deformed segment intermediate the ends thereof, is next coated with any suitable non-conductive bioabsorbable material. Preferred bioabsorbable materials include polymers prepared from organic monomers such as glycosides; a L-lactide; a D-lactide; a meso-lactide; 1,4-dioxan-2-one, trimethylene carbonate; and e-caprolactone. Additional details concerning these bioabsorbable materials and processes for applying them appear in U.S. Pat. Nos. 4,490,326, 4,878,890, 5,468,253 and 5,713,920, all of which are incorporated herein by reference. Briefly, the coating process can involve either a dipping operation or a vacuum gas phase deposition operation.

While the electrode wire 26 could be a solid (i.e., single filament) piece of wire made from any suitable electrically conductive medical grade material, the use of multi-strand braided or twisted wire is beneficial because of its enhanced flexibility, which facilitates insertion into a patient's heart 12 and thereby reduces heart trauma. Also, while the use of a bioabsorbable coating is desirable for reasons discussed hereinafter, non-bioabsorbable coating materials, such as polyethylene, polytetrafluorethylene, silicone, and nylon, could be used, as well as electrically conductive coatings. Alternatively, the coating could be eliminated entirely, whereby the stripped and deformed portion of the electrode wire 26 would be left bare (i.e., uninsulated).

FIGS. 2–6 illustrate the structural features of the resulting anchor 20, which has a generally barbed harpoon-like shape. More particularly, the anchor 20 includes a proximal end 30 and a distal end 32, each having a generally circular transverse cross-sectional shape (see, for example, FIG. 4) which is similar to the original (i.e., undeformed) shape of the electrode wire 26. Of course, as explained above, the original electrical insulation has been removed from the electrode wire 26 and replaced with a coating 34 selected from any of the bioabsorbable materials referred to above, which may be transparent or colored. Like the original coating, the bioabsorbable coating 34 encases the electrode wire 26, except for an exposed tip 36 at the severed end of the electrode wire 26 (i.e., at the point where the electrode wire 26 is cut to remove the needle 16).

The aforementioned deformed section of the electrode wire 26 is positioned intermediate the proximal and distal ends 30, 32 and is in the shape of a flattened barb 38. More particularly, the barbed section 38 has a short leg 40 (e.g., about 5 to 25 times the diameter of the electrode wire 26), which forms an angle α with the distal end 32, and a long leg 42 (e.g., about 10 to 60 times the diameter of the electrode wire 26), which forms an angle β with the short leg 40 and an angle γ with the proximal end 30. To achieve the desired shape of the barbed section 38, the angle α is in a range of from about 60° to about 120°, while the angle β is in a range of from about 40° to about 90° and the angle γ is in a range of from about 110° to about 180°. Also, the angle α should be at least about 3° less than the angle γ and at least about 5° greater then the angle β. Regardless of the angle sizes selected, the transitions between the barbed section 38 and the proximal and distal ends 30, 32, respectively, should be as smooth as possible.

Comparing FIG. 4 to FIGS. 5 and 6, it can be seen that the undeformed portions (i.e., the proximal and distal ends 30, 32) of the electrode wire 26 have a number of strands or filaments 44 arranged to provide a generally circular transverse cross-sectional shape (see FIG. 4), the strands 44 being rearranged (during the aforementioned deformation process) into a generally rectangular transverse cross-sectional shape (see FIGS. 5 and 6). Typically, the diameter (D) of the undeformed electrode wire 26 shown in FIG. 4 is in a range of from about 0.005" to about 0.020" inclusive of the coating 34 which has a thickness in a range of from about 0.0003" to about 0.01". After deformation into the unique configuration described above, the barbed section 38 has a pair of substantially flat, planar surfaces 46, 48 lying on opposite sides of, and spaced equally from, an imaginary plane (P) passing through a central longitudinal axis of the electrode wire 26 (see FIG. 5). Referring still to FIG. 5, the barbed section 38 of the electrode wire 26 has a width (W) in a range of from about 0.3 D to about 0.9 D and a length (L) in a range of from about 1.1 D to about 1.5 D, inclusive of the coating 34 which has a thickness in a range of from about 0.0003" to about 0.01".

It should be noted that the generally rectangular cross-sectional shape depicted in FIG. 5 is not essential. Other non-circular cross-sectional shapes (e.g., oval, oblong, etc.) are acceptable, provided they are elongated along the imaginary plane (P) shown in FIGS. 4–6.

Regardless of the cross-sectional shape that is deformed into, the barbed section 38 realizes an enhanced inherent resiliency (i.e., shape memory). This is due to the fact that the deformation process compresses the strands 44 of the barbed section 38 into a tighter array or bundle. Once the bioabsorbable coating 34 is applied, the filaments 44, which are now tightly bundled, are effectively constrained to their deformed shape, at least until such time as the coating 34 begins to lose its strength retention (e.g., in about 7 to 10 days).

The braided construction of the electrode wire 26 is preferred over a solid construction because the braided construction forms a better bond with the bioabsorbable coating 34. Also, while it is preferable to make the barbed section 38 out of a continuous contiguous piece of the electrode wire 26, it could be made out of a separate piece of wire or other material, which may be either electrically conductive or electrically non-conductive, and then attached by any suitable means to the electrode wire 26.

Figure 7A:
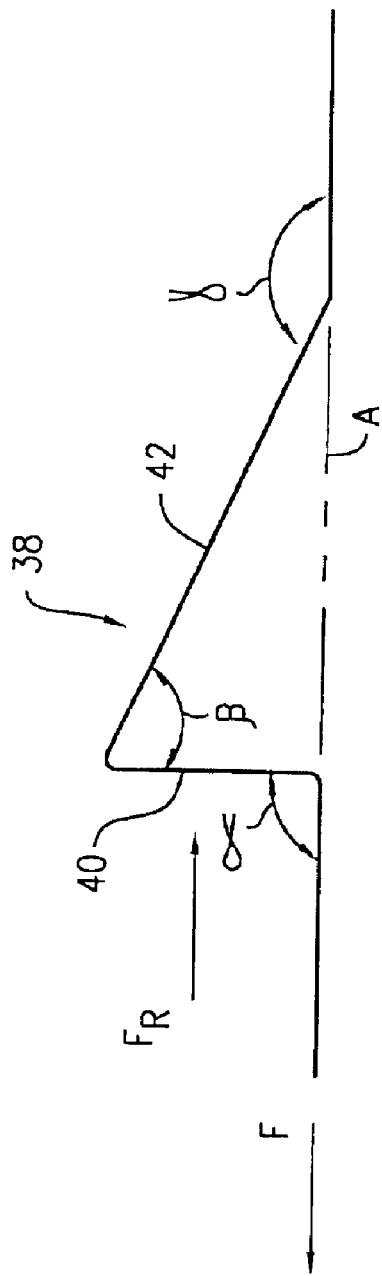
FIGS. 7a and 7b are sequential schematic representations which illustrate the snaking action of the pacing wire of FIG. 1 as it is inserted into a patient's heart.
Figure 7B:
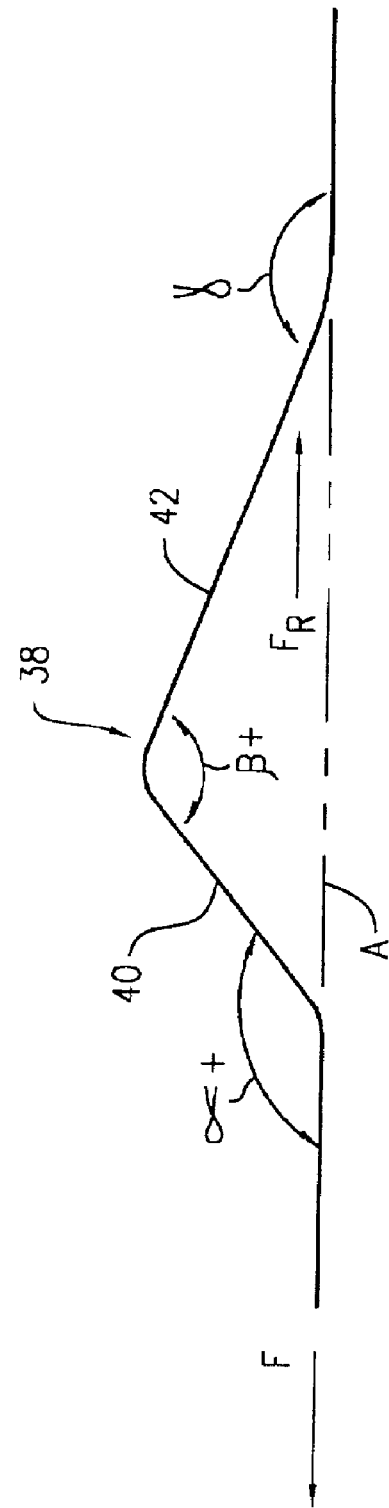

As schematically illustrated in FIGS. 7a and 7b, the size, shape and construction of the barbed section 38 cooperate to facilitate the insertion of the pacing wire 10 by achieving a "snaking" action during the insertion process. More particularly, and with reference to FIG. 7a, an insertion force (F) results in reactive forces ($F_R$) which are applied primarily against the short leg 40 of the barbed section 38, but also against the long leg 42. The reactive forces ($F_R$) cause the short and long legs 40, 42 to deflect as illustrated in FIG. 7b, thereby increasing the angles α and β to α+ and β+, respectively. The resiliency (i.e., shape memory) of the barbed section 38, which results from the deformation process described above and the natural resiliency of the coating 34, urges the short and long legs 40, 42 back toward their original positions illustrated in FIG. 7a. The cycle described above is then repeated, resulting in a "snaking" action which facilitates the insertion of the pacing wire 10 until its distal end 14 reaches the position illustrated in FIG. 1.

While still referring to FIGS. 7a and 7b, it is noted that the barbed section 38 lies entirely on one side of an axis of symmetry (A). In other words, the barbed section 38 has an asymmetrical shape relative to the axis (A). Thus, no reactive forces are being applied on the opposite side of the axis (A). If any such reactive forces existed, they would tend to impede the insertion of the pacing wire 10.

Figure 8:
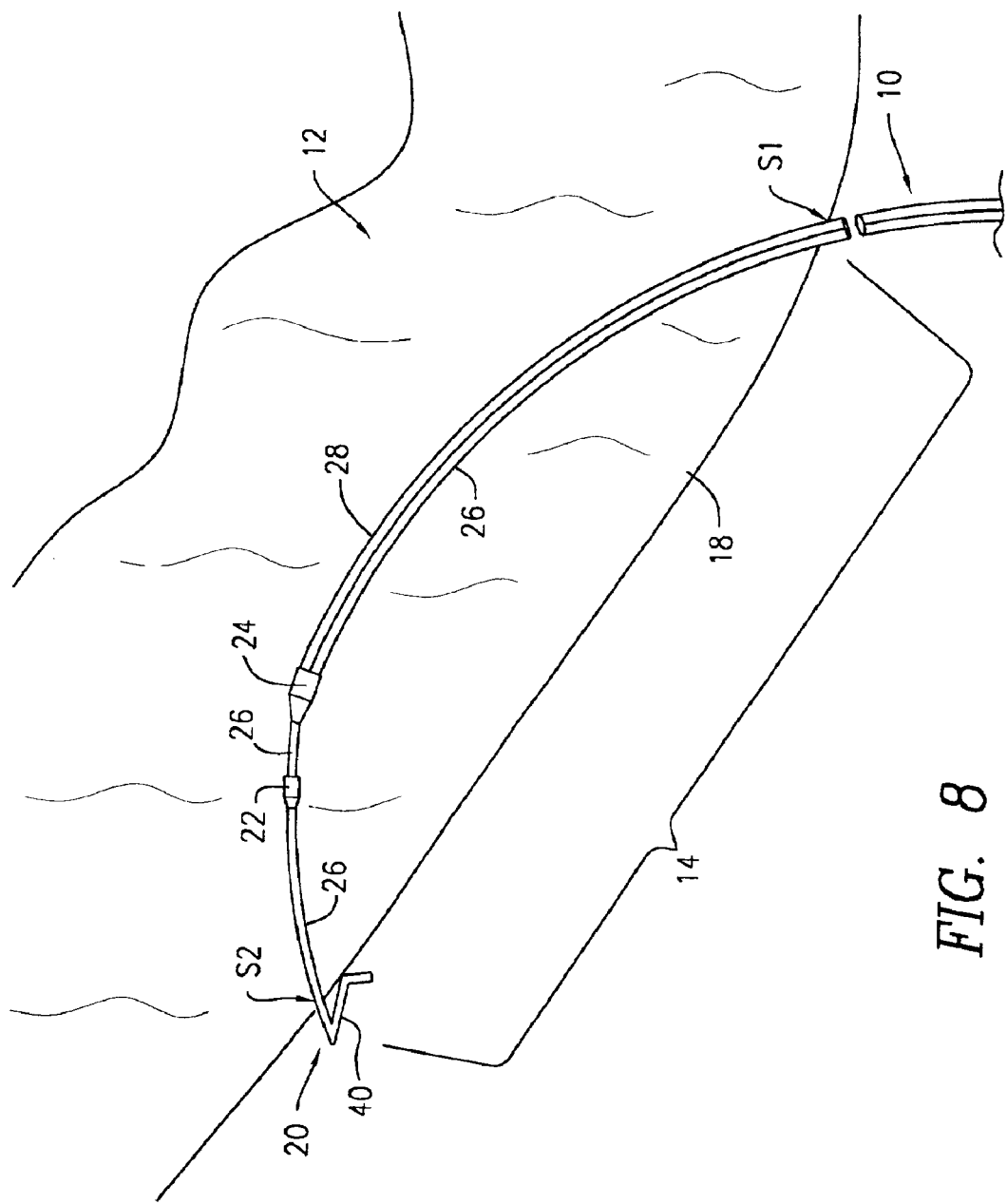
FIG. 8 is a schematic representation similar to FIG. 1, except that the anchor is shown in a position which it assumes when performing its anchoring function.

Referring back to FIG. 1, it should be remembered that the anchor 20 is positioned outside the heart 12 adjacent to the myocardium 18. In this position, any force tending to pull the distal end 14 of the pacing wire 10 back through the heart 12 will cause the anchor 20 to assume the position illustrated in FIG. 8 (i.e., a position in which the short leg 40 engages the myocardium 18), which position inhibits the inadvertent detachment of the pacing wire 10. In other words, the anchor 20 increases the retention strength or force of the pacing wire 10. As the bioabsorbable coating 34 loses its strength retention, the portion of the electrode wire 26 that is provided with the coating 34 (i.e., the portion which includes the anchor 20) becomes more flexible, thereby allowing the pacing wire 10 to be withdrawn from the heart 12 with less effort and therefore with less trauma to the heart 12. If some of the coating 34 becomes dislodged during the withdrawal of the pacing wire 10, the dislodged bioabsorbable material will actually aid in clotting and healing the exit wound.

It should be understood that the embodiment described herein is merely exemplary and that a person skilled in the art may make many variations and modifications without departing from the spirit and scope of the invention. For instance, the present invention can be used in connection with a monopolar temporary cardiac pacing wire, in which case it would be necessary to employ two pacing wires, each one having its own anchor. All such variations and modifications are intended to be included within the scope of the invention as defined in the appended claims.

What is claimed is:

1. In a temporary cardiac pacing wire which is made from an electrically conductive wire having a generally circular shape in transverse cross-section and which includes an anchor, the improvement wherein said anchor has a barbed harpoon-like shape with a single barb which is made from a flattened section of said electrically conductive wire, and wherein said anchor is coated with a bioabsorbable material.

2. The improved temporary cardiac pacing wire of claim 1, wherein said flattened section of said anchor includes a pair of substantially flat, planar surfaces lying on opposite sides of a plane containing a central longitudinal axis of said wire, whereby said barb has a generally rectangular shape in transverse cross section.

3. The improved temporary cardiac pacing wire of claim 2, wherein said flattened section of said anchor has an asymmetrical shape.

4. In a surgical electrode having an anchor, the improvement wherein said anchor is coated with a bioabsorbable material, said anchor having a barbed harpoon-like shape with a single barb, said surgical electrode being made from an electrically conductive wire having a generally circular shape in transverse cross-section, said barb being made from a flattened section of said wire, said flattened section of said anchor having an asymmetrical shape and including a pair of substantially flat, planar surfaces lying on opposite sides of a plane containing a central longitudinal axis of said wire, whereby said barb has a generally rectangular shape in transverse cross section, said wire having a multi-strand construction.

5. The improved surgical electrode of claim 4, wherein said anchor, including said barb, is constrained by said bioabsorbable coating.

6. In a temporary cardiac pacing wire which is made from an electrically conductive wire and which includes an anchor, the improvement wherein said anchor is provided with a barb made from a flattened section of said electrically conductive wire.

7. The improved temporary cardiac pacing wire of claim 6, wherein said anchor, including said barb, is coated with a bioabsorbable material.

8. The improved temporary cardiac pacing wire of claim 7, wherein said bioabsorbable material is a polymer made from an organic monomer.

9. The improved temporary cardiac pacing wire of claim 8, wherein said coating is selected from a group consisting of glycosides; a L-lactide; a D-lactide; a meso-lactide; 1,4-dioxan-2-one, trimethylene carbonate; and e-caprolactone.

10. The improved temporary cardiac pacing wire of claim 6, wherein said anchor has a barbed harpoon-like shape.

11. The improved temporary cardiac pacing wire of claim 10, wherein said anchor has a single barb.

12. The improved temporary cardiac pacing wire of claim 11, wherein said temporary cardiac pacing wire is made from said electrically conductive wire having a generally circular shape in transverse cross-section.

13. In a surgical electrode having an anchor, the improvement wherein said anchor has a harpoon-like shape with a single barb, said surgical electrode being made from an electrically conductive wire having a generally circular shape in transverse cross-section, said barb being made from a flattened section of said wire, said flattened section of said anchor having an asymmetrical shape and including a pair of substantially flat, planar surfaces lying on opposite sides of a plane containing a central longitudinal axis of said wire, whereby said barb has a generally rectangular shape in transverse cross section, said flattened section of said anchor, said wire having a multi-strand construction.

14. The improved surgical electrode of claim 13, wherein said anchor, including said barb, is constrained by said bioabsorbable coating.

15. The improved surgical electrode of claim 14, wherein said surgical electrode is a temporary cardiac pacing wire.

* * * * *